United States Patent [19]

Parodi

[11] Patent Number: 5,709,701
[45] Date of Patent: Jan. 20, 1998

[54] APPARATUS FOR IMPLANTING A PROTHESIS WITHIN A BODY PASSAGEWAY

[76] Inventor: Juan C. Parodi, Mercedes 4255, Buenos Aires, Argentina, 1419

[21] Appl. No.: 644,684

[22] Filed: May 30, 1996

[51] Int. Cl.⁶ ............................................ A61M 29/00
[52] U.S. Cl. ................................... 606/194; 623/1
[58] Field of Search .......................... 606/198, 194, 606/191, 195; 623/1, 12

[56] References Cited

U.S. PATENT DOCUMENTS

| | | | |
|---|---|---|---|
| 3,657,744 | 4/1972 | Ersek | 3/1 |
| 4,140,126 | 2/1979 | Choudhury | 128/325 |
| 4,562,596 | 1/1986 | Kornberg | 623/1 |
| 4,577,631 | 3/1986 | Kreamer | 128/334 R |
| 4,733,665 | 3/1988 | Palmaz | 128/343 |
| 4,787,899 | 11/1988 | Lazarus | 623/1 |
| 5,104,399 | 4/1992 | Lazarus | 623/1 |
| 5,219,355 | 6/1993 | Parodi et al. | 606/191 |
| 5,316,023 | 5/1994 | Palmaz et al. | 606/198 |
| 5,571,171 | 11/1996 | Barone et al. | 623/1 |
| 5,571,173 | 11/1996 | Parodi | 623/1 |
| 5,578,071 | 11/1996 | Parodi | 623/1 |

*Primary Examiner*—Michael Buiz
*Assistant Examiner*—Kevin Truong
*Attorney, Agent, or Firm*—Tobor & Goldstein L.L.P.

[57] ABSTRACT

An apparatus for repairing a body passageway, includes a catheter having first and second inflatable portions, a prosthesis having first and second ends, and a first securing member associated with the first end of the prosthesis and disposed on the second inflatable portion of the catheter. A method of assembling the apparatus for repairing a body passageway, a method of repairing a body passageway, and a method for implanting a prosthesis are also described.

4 Claims, 3 Drawing Sheets

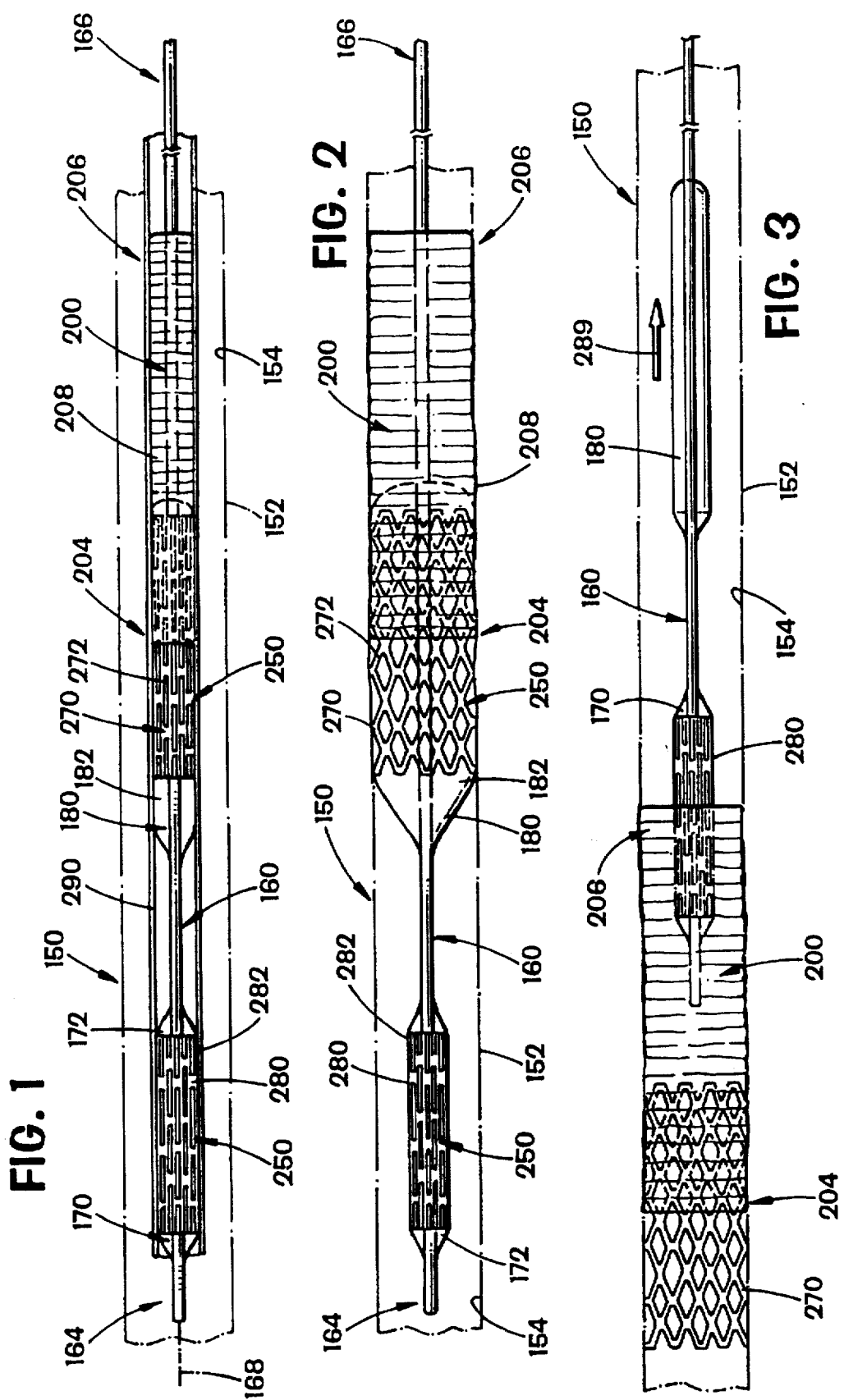

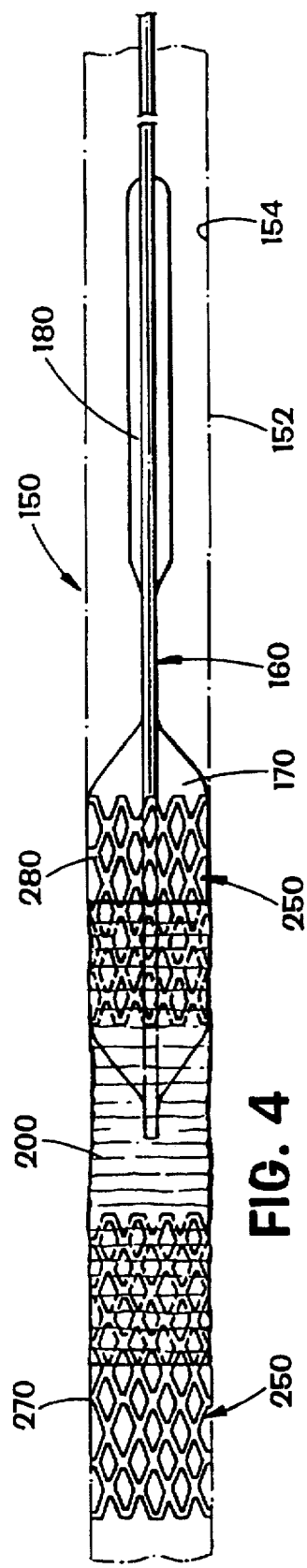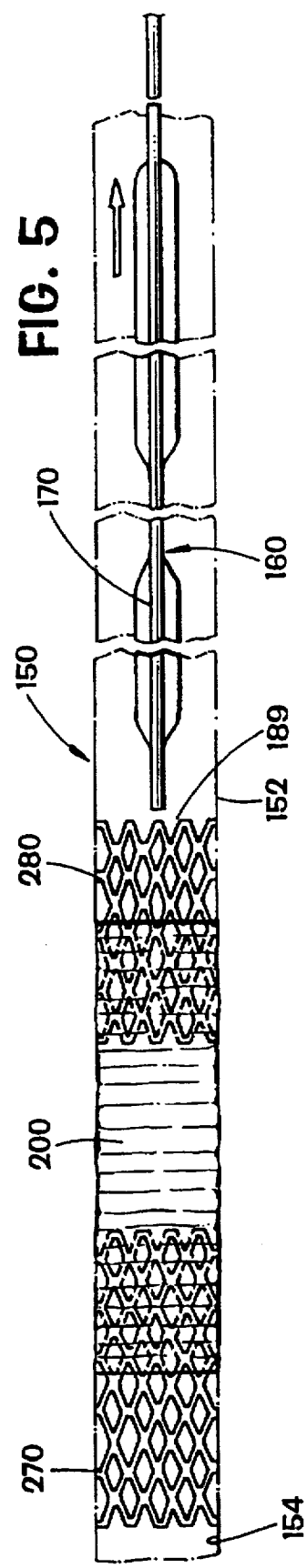

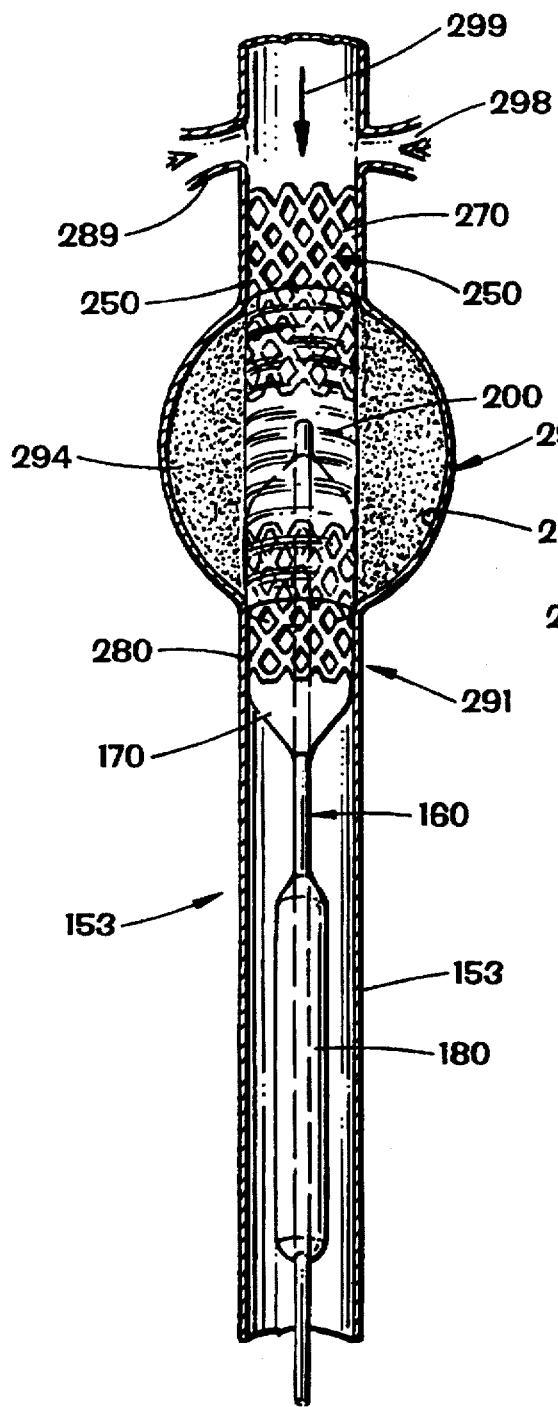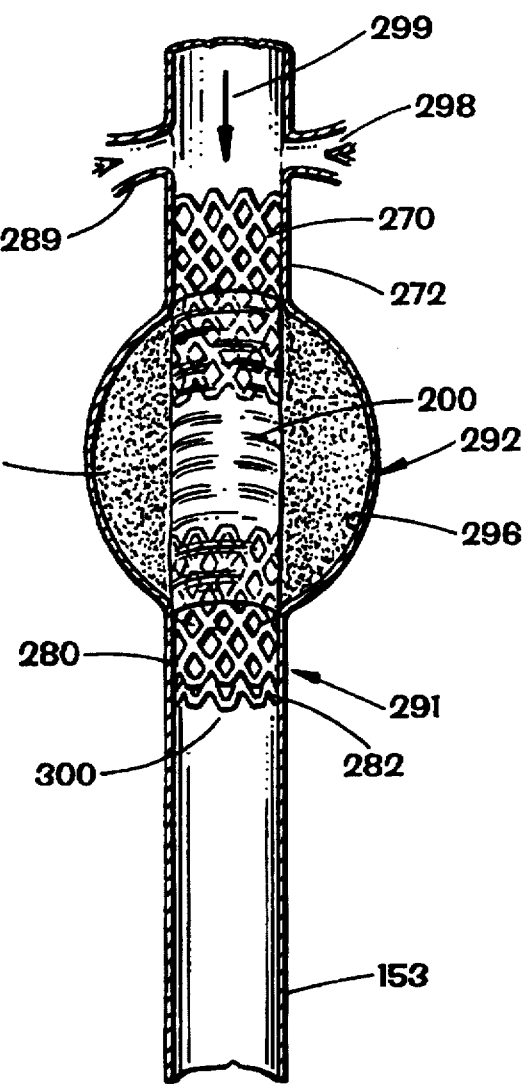

APPARATUS FOR IMPLANTING A PROTHESIS WITHIN A BODY PASSAGEWAY

BACKGROUND OF THE INVENTION

1. Field of the Invention

This invention relates to an apparatus and method for implanting a prosthesis in a body passageway, a method for repairing a body passageway and a method for assembling an apparatus for repairing a body passageway.

2. Description of the Prior Art

Various types of surgical procedures for repairing or reinforcing body passageways require the use of catheters. It is well known that catheters, having inflatable portions, or balloons, are used to implant prosthesis, or grafts, in arteries, ureters and other body passageways. For such implantations, the inflatable portion of a catheter may be used to expand and deform a first attachment device, or securing means, disposed about the balloon and associated with the first end of the prosthesis, by subjecting the attachment device, or securing means, to expansion forces by inflation of the balloon. Upon deflation of the balloon, the first attachment device and prosthesis remain secured within the body passageway. The catheter is then removed from the body passageway and a second attachment device may be placed about the catheter balloon. The catheter is reintroduced into the body passageway for securing the second end of the prosthesis to the body passageway with the second attachment device. Alternatively, a second catheter with a second attachment device is introduced. Upon removal of the catheter from the body passageway, the first and second attachment devices, or securing means, and prosthesis remain anchored to the internal wall of the body passageway. A disadvantage of the prior art techniques is the necessary surgery time for twice inserting a catheter to secure the prosthesis within the body passageway.

The use of catheters with two inflatable balloons for implanting a prosthesis is also known in the prior art. Typically, an attachment device, or securing means, is associated with each end of the prosthesis and is disposed about each catheter balloon for placement within the body passageway. The first, or upstream, end of the prosthesis and first attachment device are disposed about the distal, or outermost, balloon, while the second, or downstream, end of the prosthesis and second attachment device are associated with the proximal balloon. The catheter, prosthesis and attachment devices are introduced into the body passageway and the balloons are expanded to secure the attachment devices and prosthesis within the body passageway.

A potential disadvantage of prior art multi-balloon catheters is that the prosthesis may be implanted without being urged across its entire length toward the interior wall surface of the body passageway to remove or reduce kinking, twisting and/or folding of the prosthesis to ensure a clear, open passageway through the prosthesis within the body passageway. Another potential disadvantage of the prior art devices is that the second attachment device, or securing means, cannot be selectively positioned at any location within the prosthesis after the first attachment device, or securing means, and first end of the prosthesis have been secured within the body passageway.

Accordingly, prior to the development of the present invention, there has been no apparatus for repairing a body passageway, method of assembling such an apparatus, method of repairing a body passageway and method of implanting a prosthesis within a body passageway with the use of such an apparatus, which: allows for the prosthesis to be urged across its entire length toward the interior wall surface of the body passageway to remove or reduce kinking, twisting and/or folding of the prosthesis to ensure a clear, open passageway through the prosthesis within the body passageway; and allows for the second attachment device, or securing means, to be selectively positioned at any location within the prosthesis after the first attachment device, or securing means, and first end of the prosthesis have been secured within the body passageway. Therefore, the art has sought an apparatus for repairing a body passageway, method of assembling such an apparatus, method of repairing a body passageway and method of implanting a prosthesis within a body passageway with the use of such an apparatus, which: is believed to allow for the prosthesis to be urged across its entire length toward the interior wall surface of the body passageway to remove or reduce kinking, twisting and/or folding of the prosthesis to ensure a clear, open passageway through the prosthesis within the body passageway; and is believed to allow for the second attachment device, or securing means, to be selectively positioned at any location within the prosthesis after the first attachment device, or securing means, and first end of the prosthesis have been secured within the body passageway.

SUMMARY OF THE INVENTION

In accordance with the invention, the foregoing advantages have been achieved through the present method and apparatus for implanting a prosthesis within a body passageway. The apparatus of the present invention may include: a catheter having first and second ends, the first end of the catheter being insertable into the body passageway, a first inflatable portion disposed on the catheter proximate the first end of the catheter, and a second inflatable portion disposed on the catheter between the first inflatable portion and the second end of the catheter; a prosthesis having first and second ends; and a first means for securing the prosthesis to the body passageway, the first securing means being associated with the prosthesis proximate the first end of the prosthesis, and the first securing means and prosthesis being disposed upon the second inflatable portion of the catheter. A further feature of the present invention is that the first and second inflatable portions may be first and second inflatable balloons.

Further features of the present invention may include: the inclusion of a second means for securing the prosthesis to the body passageway disposed upon the first inflatable member; and the first and second means for securing being first and second expandable tubular shaped members.

In accordance with the invention, the foregoing advantages have also been achieved through the present method of assembling an apparatus, having a catheter with first and second inflatable members, and a prosthesis, for repairing a body passageway. The method of the present invention may include the steps of: associating a first means for securing, the prosthesis within the body passageway, with the prosthesis, proximate the first end of the prosthesis; disposing the first securing means and the first end of the prosthesis about the second inflatable member of the catheter; and disposing a second means for securing the prosthesis within the body passageway about the first inflatable member of the prosthesis. A further feature of the present invention may include the step of providing a delivery sheath about the catheter, prosthesis and the first and second securing means.

In accordance with the invention the foregoing advantages have also been achieved through the present method of repairing a body passageway having an interior wall surface with an elongate, tubular shaped prosthesis and a catheter having first and second ends, a first inflatable member disposed on the catheter proximate the first end of the catheter, a second inflatable member disposed on the catheter between the first inflatable member and the second end of the catheter. The method of the present invention may include the steps of: providing a first means, for securing the prosthesis within the body passageway to the prosthesis, proximate the first end of the prosthesis; providing the first securing means and the first end of the prosthesis about the second inflatable member; introducing the catheter, having the first securing means and prosthesis disposed thereon, into the body passageway; positioning the second inflatable member of the catheter at a desired location within the body passageway; securing the first securing means and the prosthesis within the body passageway by inflating the second inflatable member; deflating the second inflatable member; and removing the catheter from the body passageway.

A further feature of the present invention may include the steps of at least partially deflating the second inflatable member and moving the second inflatable member from the first end toward the second end of the prosthesis, to urge the prosthesis toward the interior wall surface of the body passageway. A further feature of the present invention may include the steps of: disposing a second securing means upon the first inflatable member; selectively positioning the first inflatable member within the prosthesis while the prosthesis is located in the body passageway; and securing the second securing means and the prosthesis within the body passageway by inflating the first inflatable member.

Another aspect of the present invention is a method of implanting, within a body passageway, a prosthesis, having first and second ends, the first end of the prosthesis being associated with a first securing means, by use of a catheter, the catheter having first and second ends, a longitudinal axis extending therebetween, and first and second inflatable portions, the first inflatable portion being disposed proximate the first end of the catheter, the second inflatable portion being disposed between the first inflatable portion and the second end of the catheter, the first end of the prosthesis and the first securing means being disposed on the second inflatable portion of the catheter, and a second securing means being disposed upon the first inflatable portion of the catheter. The method of the present invention may include the steps of: delivering the catheter, the prosthesis and the first and second securing means into the body passageway; inflating the second inflatable portion of the catheter to expand the first securing means and to anchor the first securing means and first end of the prosthesis within the body passageway; at least partially deflating the second inflatable portion of the catheter; moving the second inflatable portion through the prosthesis; positioning the first inflatable portion at a desired location at least partially within the prosthesis; inflating the first inflatable portion to expand the second securing means, and anchoring the second securing means and the prosthesis within the body passageway; deflating the first inflatable portion; and removing the catheter from the body passageway. A further feature of the present invention may include the step of utilizing, as the first and second securing means, first and second expandable tubular shaped members.

The methods and apparatus for repairing a body passageway of the present invention, when compared with previously proposed prior art devices and methods for repairing body passageways, are believed to have the advantages of: allowing the prosthesis to be urged across its entire length toward the interior wall surface of the body passageway to remove or reduce kinking, twisting and/or folding of the prosthesis to ensure a clear, open passageway through the prosthesis within the body passageway; allowing the second attachment device, or securing means, to be selectively positioned at any location within the prosthesis after the first attachment device, or securing means, and first end of the prosthesis have been secured within the body passageway.

BRIEF DESCRIPTION OF THE DRAWINGS

In the drawings:

FIG. 1 is a partial cross-sectional view of the apparatus of the present invention disposed in a body passageway;

FIG. 2 is a partial cross-sectional view of the apparatus of the present invention within a body passageway, illustrating a second inflatable portion of a catheter in an inflated configuration;

FIG. 3 is a partial cross-sectional view of an apparatus of the present invention within a body passageway after a first securing means and the first end of a prosthesis are secured within the body passageway;

FIG. 4 is a cross-sectional view of the apparatus of the present invention, within a body passageway, having a second inflatable portion in its expanded configuration;

FIG. 5 is a partial cross-sectional view of the apparatus of the present invention within a body passageway after a prosthesis has been implanted in the body passageway;

FIG. 6 is a partial cross-sectional view of an abdominal aortic aneurysm in the process of being repaired in accordance with the present invention; and FIG. 7 is a partial cross-sectional view of the abdominal aortic aneurysm of FIG. 6, illustrating a prosthesis and securing means anchored in the body passageway in accordance with the present invention.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

In FIGS. 1–6, an apparatus 150 for repairing a body passageway 152, such as an artery (153, FIGS. 6–7) or ureter, is shown. Generally, the apparatus 150 includes: a catheter 160 having at least two inflatable portions 170, 180; a prosthesis, or graft, 200; and means for securing 250 the prosthesis, or graft, 200 within the body passageway 152.

The catheter 160 of the present invention may be any known type of intraluminally deliverable catheter having at least two inflatable portions, such as the balloon device disclosed in U.S. Pat. No. 5,219,355 issued on Jun. 15, 1993, to Juan C. Parodi and Hector D. Barone, incorporated herein by reference. With reference to FIG. 1, the catheter 160 includes first and second ends 164, 166, respectively, and a longitudinal axis 168 extending therebetween, the first end 164 being insertable into the body passageway 152.

For purposes of illustration, catheter 160 is shown in FIGS. 1–5 to include first and second inflatable portions 170, 180 disposed on the catheter 150 along its longitudinal axis 168 (FIG. 1), although there is no limit as to the number of inflatable portions that may be included on the catheter in the present invention. The first inflatable portion 170 of the catheter 160 is disposed on the catheter 160 proximate the first end 164 of the catheter 160, while the second inflatable portion 180 is disposed on the catheter 160 between the first inflatable portion 170 and the second end 166 of the catheter 160. The inflatable portions 170, 180 may be any known type of inflatable devices used in connection with catheters and capable of being inflated and deflated while located within a body passageway, such as balloons 172, 182 (FIG. 2).

With further reference to FIGS. 1–2, the apparatus 150 may include a prosthesis, or graft, 200 for delivery to the body passageway 152, and a means for securing 250 the prosthesis 200 within the body passageway 152. The prosthesis, or graft, 200 has first and second ends 204, 206 and a wall surface 208 disposed therebetween, the prosthesis, or graft, 200 adapted to be disposed within the body passageway 152, such as the tubular graft described in U.S. Pat. No. 5,360,443, issued on Nov. 1, 1994 to Hector D. Barone, Julio C. Palmaz and Juan C. Parodi, which is incorporated herein by reference.

In the preferred embodiment of FIGS. 1–2, the means for securing 250 the prosthesis, or graft, 200 within the body passageway includes first and second securing means 270, 280. First and second securing means 270, 280 may each be at least one expandable tubular shaped member 272, 282. Any known type of intraluminally deliverable expandable member, or stent, could be utilized as first and second securing means 270, 280, provided it has the ability to be secured to a prosthesis, carried on an inflatable member of a catheter for delivery into a body passageway and expanded to secure the expandable member and prosthesis to the interior wall of a body passageway. An example of an expandable tubular shaped member suitable for use in the present invention is shown in U.S. Pat. No. 4,773,665, issued Mar. 29, 1998 to Julio C. Palmaz and incorporated herein by reference.

As shown in FIGS. 1 and 2, first securing means 270 is preferably associated with the first end 204 of the prosthesis 200 and releasably mounted upon the second inflatable member 180 for delivery into the body passageway 152. The first securing means 270 and first end 204 of the prosthesis 200 may be associated in any suitable manner, such as with small sutures. After the first securing means 270 and first end 204 of the prosthesis 200 are disposed on the second inflatable member 180, the second end 206 of the prosthesis 200 will extend over the catheter 160 in the direction of the second end 166 of the catheter 160. The second securing means 280 may be releasably mounted upon the first inflatable member 170 for delivery to the body passageway 152 and for further securing the prosthesis 200 within the body passageway 152, as will be hereinafter described in further detail. Each of the first and second securing means 270, 280 may be disposed upon the inflatable members 170, 180 in any suitable fashion, whereby upon inflation of the respective inflatable members, the associated securing means and prosthesis are forced radially outwardly into contact with the interior wall 154 of the body passageway 152. A delivery sheath 290 (FIG. 1) may be provided about the catheter 160, the prosthesis 200 and the first and second securing means 270, 280 for delivery into the body passageway 152.

With further reference to FIG. 1, a method of assembling the apparatus 150, as described above, for repairing a body passageway 152 is shown. The apparatus 150 includes a catheter 160 having at least two inflatable portions 170, 180, a prosthesis 200, and first and second means for securing 270, 280 the catheter 160 within the body passageway 152. The method of assembling includes the step of associating the first securing means 270 with the prosthesis 200 proximate the first end 204 of the prosthesis 200. The first securing means 270 and first end 204 of the prosthesis 200 may be associated in any suitable manner, such as with small sutures. The first securing means 270 and first end 204 of the prosthesis 200 are then disposed upon the second inflatable member 180 of the catheter 160, so that the prosthesis 200 extends over the catheter 160 in the direction of the second end 166 of the catheter 160. The second means for securing 280 the prosthesis 200 within the body passageway 152 is disposed upon the first inflatable member 170. Each of the first and second securing means 270, 280 may be disposed upon the inflatable members 170, 180 in any suitable manner, whereby upon inflation of the respective inflatable members, the associated securing means and prosthesis are forced radially outwardly into contact with the interior wall 154 of the body passageway 152. The method of assembling may include the further step of providing a conventional delivery sheath 290 about the catheter 160, prosthesis 200 and securing means 250, which is removed as the catheter 160 is disposed within the body passageway 152.

With reference to FIGS. 1–3, a method of repairing a body passageway 152, having an interior wall surface 154, with an elongate, tubular shaped prosthesis 200 and a catheter 160 is shown. The catheter 160, as described above, has first and second ends 164, 166, a first inflatable member 170 disposed on the catheter proximate the first end 164 of the catheter 160, and a second inflatable member 180 disposed on the catheter 160 between the first inflatable member 170 and the second end 166 of the catheter 160.

A first means 270 for securing the prosthesis 200 within the body passageway 152, as described above, is provided proximate the first end 204 of the prosthesis 200. The first securing means 270 and the first end 204 of the prosthesis 200 are provided disposed upon the second inflatable member 180 of the catheter 160. The catheter 160, having the first securing means 270 and prosthesis 200 disposed thereon, is introduced into the body passageway 152 and selectively positioned therein, using conventional techniques. By first inflating the second inflatable member 180, the first securing means 270 may be expanded to secure the first securing means 270 and prosthesis 280 within the body passageway (FIG. 2).

As shown in FIG. 3, the method of repairing a body passageway 152 may include the further step of at least partially deflating the second inflatable member 280 and moving the second inflatable member 280 in the direction of arrow 289 from the first end 204 toward the second end 206 of the prosthesis 200 to urge the prosthesis 200 toward the interior wall surface 154 of the body passageway 152. As a result, any kinking, twisting and/or folding in the prosthesis 200 will be removed or reduced, enhancing the fit of the prosthesis 200 within the body passageway 152 and optimizing the effect of the prosthesis 200 as a fluid passageway (189 FIG. 5) within the body passageway 152.

The method of repairing a body passageway 152 may also include the step of disposing a second securing means 280 upon the first inflatable member 170 (FIGS. 1–3) prior to the introduction the catheter 160 within the body passageway 152. As shown in FIG. 3, after the catheter 160 is introduced into the body passageway 152 and the first securing means 270 and first end 204 of the prosthesis 200 are secured within the body passageway 152, the catheter 160 may be moved to selectively position the first inflatable member 170 and second securing means 280 within the prosthesis 200.

The second securing means 280 may be expanded (FIG. 4) to secure the second securing means 280 and the prosthesis 200 within the body passageway 152 by inflating the first inflatable member 170. The first inflatable member 170 may then be deflated, and the catheter 160 may be removed from the body passageway 152 (FIG. 5). After the first and second securing means 270, 280 and prosthesis 200 are released from the catheter 160, the prosthesis 200 provides a passageway 189 (FIG. 5) through the body passageway 152 so that the body fluid flowing through the body passageway 152 can pass through the prosthesis 200.

A method of implanting a prosthesis 200, having first and second ends 204, 206, within a body passageway 152 (FIGS. 1–5), at a location of repair, such as an arterial aneurysm 292 (FIGS. 6–7), with an apparatus 150 will be described. As shown in FIG. 1, a first securing means 270 is associated with the first end 204 of the prosthesis 200, and the first securing means 270 and first end 204 of the prosthesis 200 are disposed on a second inflatable portion 180 of a catheter 160 of the apparatus 150. A second securing means 280 is disposed on a first inflatable portion 170 of the catheter 160. First and second expandable tubular shaped members 272, 282 (FIGS. 1 and 2) may be utilized as first and second securing means 270, 280. A conventional delivery sheath 290 (FIG. 1) may be provided about the catheter 160, the prosthesis 200 and the first and second securing means 270, 280 for delivery into the body passageway 152. The catheter 160, as illustrated in FIG. 1, is in the configuration it would have for intraluminal delivery.

The catheter 160, prosthesis 200 and first and second securing means 270, 280 are delivered, in a conventional manner, into the body passageway 152, and selectively positioned proximate a desired area of implantation of the prosthesis 200, such as aneurism 292 (FIGS. 6–7). The catheter sheath 290, if included, is removed in a conventional manner. As shown in FIG. 2, the second inflatable portion 180 of the catheter 160 is inflated to expand the first securing means 270, and anchor the first securing means 270 and first end 204 of the prosthesis 200 within the body passageway 152 at a desired location. Further, the second inflatable member 180 may be at least partially deflated, and the catheter 160 moved within the body passageway 152 so that the second inflatable portion 180 moves through the prosthesis 200 from the first end 204 to the second end 206 of the prosthesis 200 to remove or reduce kinks, twist or folds in the prosthesis 200 (FIG. 3).

As shown in FIG. 3, after the first securing means 270 and first end 204 of the prosthesis 200 are disposed within the body passageway 152, the catheter 160 may be moved to selectively position the first inflatable portion 170 and second securing means 280 at a desired location at least partially within the prosthesis 200. The first inflatable portion 170 may be inflated (FIGS. 4 and 6) to expand the second securing means 280 and secure the second securing means 280 and prosthesis 200 within the body passageway 152. The first inflatable portion 170 of the catheter 160 may then be deflated and the catheter 160 removed from the body passageway 152, as shown in FIG. 5.

FIGS. 6 and 7 illustrate the use of the apparatus 150 and methods of the present invention to repair an abdominal aortic aneurism 292 in an aorta 291. The apparatus 150 could also be utilized in the thoracic aorta, and can be used to repair thoracic aneurysms or thoracic dissecting aneurysms. Accordingly, use of the term "aortic aneurism" in this specification is intended to relate to and mean both abdominal aortic aneurysms and thoracic aneurysms. As shown, the areas of thrombosis 294 is disposed against the interior wall surface 296 of the aorta 291. Associated with the aorta 291, above aneurism 292, are a plurality of renal arteries, 298 in fluid communication with aorta 291. Blood flows through the aorta 291 in the direction of arrow 299. The prosthesis 200 provides a passageway 300 through the abdominal aortic, or arterial, aneurysm, 292, so that blood can pass through the aneurysm 292 and be separated therefrom. As seen in FIG. 6, the existing aortic wall 296 and the thrombosis 294 may provide additional support and reinforcement for the prosthesis 200.

The apparatus 150 of the present invention and methods for assembling the apparatus 150, repairing a body passageway 152 and implanting a prosthesis 200 in the body passageway 152 are believed to be useful to repair or reinforce numerous types of body passageways 152 including abdominal aortic aneurysms, arterial venous fistulas, false aneurysms, ureters, and may be useful in dissection procedures, treatment of trauma-injury of arteries, and to provide internal bypasses.

It is to be understood that the invention is not limited to the exact details of construction, operation, exact materials or embodiments shown and described, as obvious modifications and equivalents will be apparent to one skilled in the art. For example, the catheter of the apparatus could be provided with three inflatable portions, two of which may be used to urge the prosthesis against the interior wall of the body passageway and remove or reduce kinks, twists and/or folds in the prosthesis. Accordingly, the invention is therefore to be limited only by the scope of the appended claims.

I claim:

1. An apparatus for repairing a body passageway, comprising:

a catheter having first and second ends, the first end of the catheter being insertable into the body passageway, a first inflatable portion disposed on the catheter proximate the first end of the catheter, and a second inflatable portion disposed on the catheter between the first inflatable portion and the second end of the catheter;

a prosthesis having first and second ends; and a first means for securing the prosthesis to the body passageway, the first securing means being associated with the prosthesis proximate the first end of the prosthesis, and the first securing means and prosthesis being disposed upon the second inflatable portion of the catheter.

2. The apparatus of claim 1, wherein the first and second inflatable portions are first and second inflatable balloons.

3. The apparatus of claim 1, further including a second means for securing the prosthesis to the body passageway, the second securing means being disposed upon the first inflatable portion.

4. The apparatus of claim 3, wherein the first and second means for securing are first and second expandable tubular shaped members.

* * * * *

UNITED STATES PATENT AND TRADEMARK OFFICE
CERTIFICATE OF CORRECTION

PATENT NO.   : 5,709,701

DATED        : January 20, 1998

INVENTOR(S)  : Juan C. Parodi

It is certified that error appears in the above-identified patent and that said Letters Patent is hereby corrected as shown below:

In the title on the cover page and in line 2 of Column 1, delete "Prothesis", and insert--Prosthesis--.

Signed and Sealed this

Fifth Day of May, 1998

Attest:

BRUCE LEHMAN

Attesting Officer

Commissioner of Patents and Trademarks